United States Patent [19]

Kohn

[11] Patent Number: 4,988,336

[45] Date of Patent: Jan. 29, 1991

[54] ELECTRONIC SUCTION REGULATOR

[75] Inventor: Gabriel S. Kohn, Ballwin, Mo.

[73] Assignee: Allied Healthcare Products, Inc., St. Louis, Mo.

[21] Appl. No.: 410,862

[22] Filed: Sep. 22, 1989

[51] Int. Cl.$^5$ .............................................. A61M 5/30
[52] U.S. Cl. .................................... 604/67; 604/119; 604/246; 604/317
[58] Field of Search ................ 604/22, 30, 31, 35, 604/50, 51, 65, 67, 118–121, 246, 245, 317–326; 128/766; 290/43, 53

[56] References Cited

U.S. PATENT DOCUMENTS

| | | | |
|---|---|---|---|
| 3,429,313 | 2/1969 | Romanelli | 604/35 X |
| 3,693,027 | 6/1976 | Muriot | 604/120 |
| 4,024,866 | 5/1977 | Wallach | 604/22 X |
| 4,117,843 | 10/1978 | Banko | 604/65 X |
| 4,303,072 | 12/1981 | Lewis | 604/119 |
| 4,324,243 | 4/1982 | Helfgott et al. | 605/22 X |
| 4,395,258 | 7/1983 | Wang et al. | |
| 4,511,806 | 4/1985 | May | 290/43 |
| 4,622,503 | 11/1986 | Sundblom et al. | 604/22 X |
| 4,650,460 | 3/1987 | Roizenblatt | 604/22 |
| 4,654,029 | 3/1987 | D'Antonio | |
| 4,678,922 | 7/1987 | Leininger | |
| 4,706,687 | 11/1987 | Rogers | |
| 4,740,202 | 4/1988 | Stacey et al. | |
| 4,795,428 | 1/1989 | Hwang | 604/73 |
| 4,810,242 | 3/1989 | Sundblom et al. | |

Primary Examiner—C. Fred Rosenbaum
Assistant Examiner—Adam J. Cermak
Attorney, Agent, or Firm—Dickstein, Shapiro & Morin

[57] ABSTRACT

An electronic vacuum suction regulator for regulating the vacuum applied to a patient is disclosed in which the vacuum source generally present in patient rooms in a hospital is utilized to drive an air motor which is connected to an AC generator to produce an alternating current which is then converted to a regulated DC current and used to operate a microprocessor and associated circuitry. The programmed microprocessor operates an electrical valve which turns the suction vacuum to the patient on and off and also provides a display of desired parameters by means of a lighted LCD display. The microprocessor may be programmed by means of an on-board keyboard.

22 Claims, 1 Drawing Sheet ic SUCTION REGULATOR

BACKGROUND OF THE INVENTION

The present invention relates to apparatus for the control of vacuum suction used with medical devices in order to aspirate fluids and gases that collect in body cavities of patients. More particularly, the present invention relates to an electronic suction regulator for regulating the vacuum suction generally available in hospitals for use in aspirating fluids and gases that collect in body cavities of patients because of injury, disease or surgery.

The use of vacuum suction regulators as medical devices is well known for aspirating fluids and gases from patients in hospitals. Generally, such vacuum suction regulators attach to a vacuum outlet in the wall of a patient's hospital room. Known vacuum suction regulators include a variable vacuum regulator, a vacuum gauge and a mechanical mechanism which cycles the vacuum on and off at predetermined time intervals. Such known vacuum suction regulators are mechanical devices. They utilize the vacuum source as a means of powering the cycling mechanism. In addition, although such known mechanical vacuum suction regulators are field adjustable, the intervals over which they may cycle the vacuum on and off are set at the factory to, for example, 18 seconds on and 8 seconds off. One such type of known mechanical vacuum suction regulator is that marketed under the name VACUTRON by the assignee of the instant application.

Such known mechanical vacuum suction regulators achieve vacuum cycling by means of precise air flow rates into and out of an air chamber. That chamber includes a rubber diaphragm which allows the volume in the chamber to increase and decrease on a periodic basis. The diaphragm is connected to a mechanism that cycles the vacuum on and off. In order to control the on/off time periods, two needle valves control the air flow into and out of the diaphragm. Problems arise with such known devices due to the fact that the on/off time periods are fairly long and total air chamber volume quite small. Therefore, in order to operate at such small flow rates, the valve openings themselves are also small. The small valve openings make the timing of the vacuum suction regulator sensitive to clogging by means of small dirt particles in the vacuum line.

Other types of known mechanical vacuum suction regulators also utilize vacuum as a means to power the suction regulator, however, they are operated by a pneumatic logic type system. However, such devices also are subject to becoming clogged by means of small dirt particles.

In order to reduce the negative characteristics of the known mechanically-operated vacuum driven vacuum suction regulator systems, their manufacturers have installed micron-type filters within the suction regulators in order to reduce the effect of minute dirt particles. However, the use of such filters is inconvenient since they must be replaced periodically. Another difficulty with the known mechanically operated vacuum driven vacuum suction regulators is that they are subject to being frequently dropped, thereby damaging the sensitive vacuum gauges contained within. Once dropped, it is necessary for such devices to be returned to the factory for an expensive repair.

An additional problem with the known mechanically operated vacuum suction regulators is that a certain amount of noise is generated by their operation which can be annoying to patients.

SUMMARY AND OBJECTS OF THE INVENTION

In view of the foregoing, it should be apparent that there still exists a need in the art for a vacuum suction regulator apparatus which overcomes the problems of prior art devices and which, by means of electronic circuitry, accurately controls the suction vacuum available from a distributed vacuum system such as that used in hospitals and yet is independent of contaminants contained in the air or vacuum line. It is, therefore, a primary object of this invention to provide apparatus for regulating the vacuum suction from a vacuum system in which the timing of the vacuum suction can be accurately controlled, which is characterized by simple electronic circuitry and which has particular application for use in hospitals.

More particularly, it is an object of this invention to provide an electronic vacuum suction regulator as described above in which on and off timing cycles can be easily customized to the needs of each individual patient.

Still more particularly, it is an object of this invention to provide an electronic vacuum suction regulator apparatus in which the pressure readout can be viewed directly on a lighted LCD display and which is much more rugged than the currently known mechanical type vacuum suction regulators.

Another object of the present invention is to provide an electronic vacuum suction regulator apparatus in which the noise levels during operation are vastly reduced compared to the current pneumatically driven systems.

A further object of the present invention is to provide an electronic vacuum suction regulator which can alert the hospital staff in the event that the vacuum suction lines to the patient become clogged.

Briefly described, these and other objects of the invention are accomplished by providing an electronic vacuum suction regulator in which an air motor is utilized to drive an AC generator to run the electronic circuitry of the present invention. The air motor, which may preferably be a rotary air motor, is powered by the distributed/piped vacuum in the hospital. The output shaft of the motor is connected to turn the AC generator which produces between 8 and 27 volts AC. The AC voltage is converted to a DC voltage and regulated. The DC voltage is utilized to drive the electronic circuitry of the present invention, which includes a CMOS microprocessor. The microprocessor is connected to a lighted LCD display which provides various information, such as the vacuum level and timing information, for viewing by the hospital staff. The microprocessor is programmed by means of an on-board keyboard and functions to operate an electrical valve which connects the distributed hospital vacuum source to the patient in the programmed manner. A pressure transducer is connected to the patient line to monitor the vacuum level, and is also connected to the microprocessor.

With these and other objects, advantages and features of the invention that may become hereinafter apparent, the nature of the invention may be more clearly understood by reference to the following detailed description of the invention, the appended claims an to the drawing attached herein.

DETAILED DESCRIPTION OF THE PREFERRED EMBODIMENT

Figure 1:
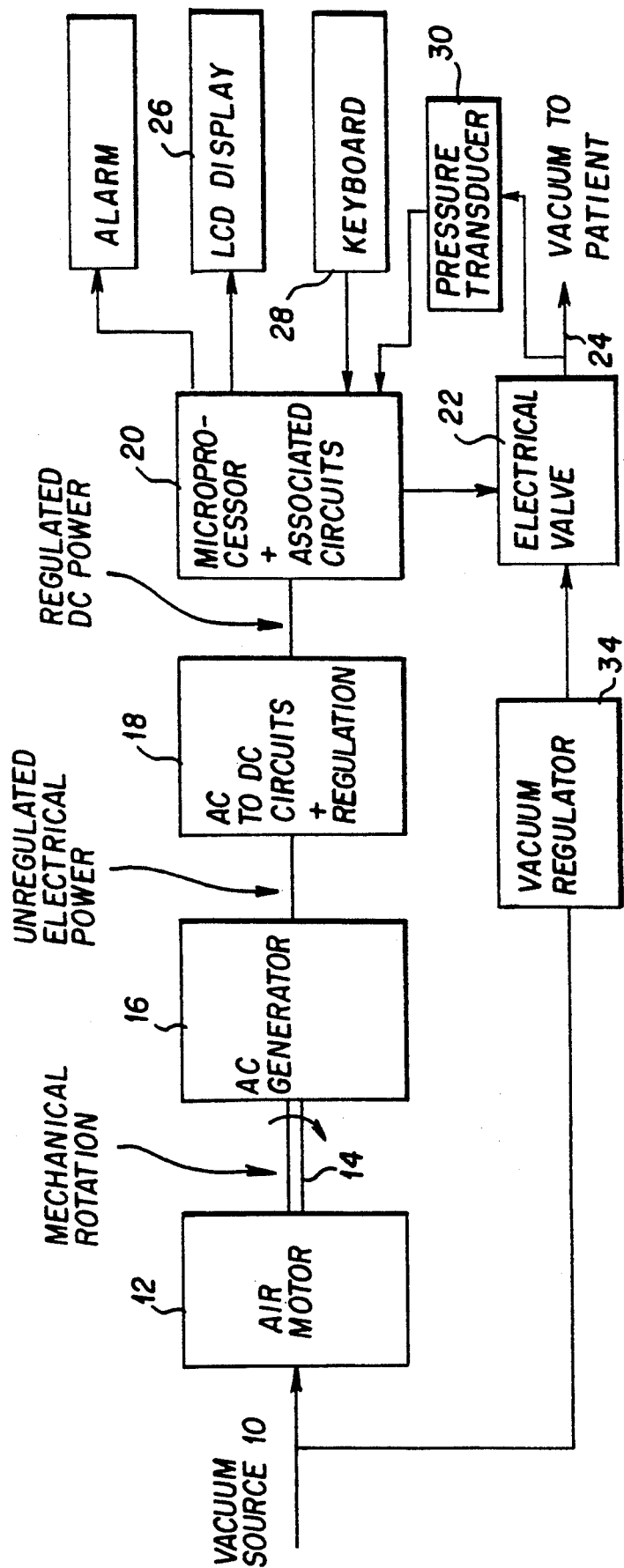
FIG. 1 is a schematic block diagram showing the apparatus of the present invention.

Referring now in detail to the drawing, there is illustrated in FIG. 1 an electronic vacuum suction regulator in which a vacuum source 10, such as that typically found in hospitals, for example, in each patient room, is connected to the input of an air motor 12. The vacuum source 10 is used to turn the motor at vacuum levels of between 9 and 28 inches of mercury.

The output shaft 14 of the air motor 12 is connected to drive an AC generator 16. Upon being rotated by the air motor 12, the AC generator 16 produces an alternating current with a voltage value of between 8 and 27 volts AC. An AC generator 16 is utilized in order to avoid potential brush sparks, which is a commonly known phenomena present with direct current generators. As will be obvious to those of ordinary skill in the art, sparks are unacceptable in a hospital environment due to the presence of oxygen and the consequent threat of a fire.

The unregulated output from the AC generator 16 is fed to an AC to DC converter circuit 18 which converts the alternating current to a direct current and which regulates the direct current to a voltage of about 5 volts. The regulated output from the AC/DC converter is provided to a microprocessor and associated circuits 20. The microprocessor may preferably be a CMOS type and includes on-board timers. These timers and the other associated circuitry are used to activate a solenoid or electrical valve 22 which is connected between the vacuum line to the patient 24 and the vacuum regulator 34 such that, under programmed control of the microprocessor 20, the desired vacuum suction is provided to the patient. The input side of the vacuum regulator 34 is connected to the vacuum source 10. The vacuum regulator may be of a mechanical, electrical or any other known type of design. The microprocessor 20 turns the vacuum provided to the patient on and off by means of its control of the electrical valve 22.

A pressure transducer 30 is connected to the patient vacuum line 24 and monitors the vacuum level on the patient line 24. The pressure transducer 30 is also connected to the microprocessor and provides its data output to the microprocessor for monitoring and control purposes.

The microprocessor is also connected to provide an output to an LCD display 26. It receives inputs from a keyboard 28. As will be known to those of ordinary skill in the art, the microprocessor can be programmed by means of the keyboard 28 and can display both the programmed and the current settings by means of the LCD display 26. Preferably, the LCD display 26 is lighted such that the nursing staff is able to monitor the vacuum regulator at night without resorting to the use of a flashlight or turning on the lights in the room.

Since the control circuitry of the present invention is electronic, the only noise produced by the device is the noise generated by the rotation of the air motor and AC generator, which is of a minimal nature, and the opening and closing of the electrical valve 22, which is also very quiet. Thus, the present invention produces vastly decreased noise levels compared to the known prior art pneumatically driven systems.

In the event that the patient vacuum line 24 becomes clogged, the microprocessor 20 can be programmed to alert the hospital staff to the problem by sounding an audible and/or visual alarm, using the alarm 32. Obviously, such alarm can be provided to a remote location, such as a nurse's station.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. An electronically controlled suction regulator, comprising:
   a source of vacuum;
   a vacuum regulator connected to said source of vacuum;
   a generator connected to be driven by said source of vacuum such that said generator produces an electrical current;
   an electrically operated valve connected to said vacuum regulator; and
   electronic circuitry powered by said electrical current for generating control signals for controlling said electrically operated valve so that said source of vacuum is supplied to a patient for predetermined periods of time.

2. The electronically controlled suction regulator of claim 1, wherein said generator includes a motor driven by said vacuum source.

3. The electronically controlled suction regulator of claim 1, wherein said generator includes an alternating current generator which is operated by said source of vacuum.

4. The electronically controlled suction regulator of claim 1, further including an AC to DC converter and regulating circuitry connected thereto such that regulated DC power is supplied to said electronic circuitry.

5. The electrically controlled suction regulator of claim 1, wherein said electronic circuitry is comprised of a programmable digital processor.

6. The electronically controlled suction regulator of claim 1, further including a lighted liquid crystal display panel connected to said electronic circuitry.

7. The electronically controlled suction regulator of claim 1, further including a keyboard connected to said electronic circuitry.

8. The electrically controlled suction regulation of claim 1, wherein said source of vacuum is between 9 and 28 inches of mercury.

9. The electrically controlled suction regulator of claim 1, wherein said source of vacuum is a hospital vacuum system.

10. The electronically controlled suction regulator of claim 1, further including a pressure transducer connected to monitor said source of vacuum applied to said patient.

11. A device for electronically regulating the suction supplied to a hospital patient, comprising:
   a source of vacuum applied to the patient's hospital room;
   a vacuum regulator connected to said source of vacuum;
   an electrical generator connected to be driven by said distributed source of vacuum to produce an electrical current;

an electrically operated valve having a vacuum input connected to said vacuum regulator and a vacuum line connected between said valve and said patient; and electronic circuitry connected to said electrically operated valve and powered by said electrical current for generating control signals for operating said electrically operated valve so that suction is applied to said patient for predetermined periods of time.

12. The electronically controlled suction regulator of claim 11, wherein said generator includes a motor driven by said vacuum source.

13. The electronically controlled suction regulator of claim 11, wherein said generator includes an alternating current generator which is operated by said source of vacuum.

14. The electronically controlled suction regulator of claim 11, further including an AC to DC converter and regulating circuitry connected thereto such that regulated DC power is supplied to said electronic circuitry.

15. The electrically controlled suction regulator of claim 11, wherein said electronic circuitry is comprised of a programmable digital processor.

16. The electronically controlled suction regulator of claim 11, further including a lighted liquid crystal display panel connected to said electronic circuitry.

17. The electronically controlled suction regulator of claim 11, further including a keyboard connected to said electronic circuitry.

18. The electrically controlled suction regulation of claim 11, wherein said source of vacuum is between 9 and 28 inches of mercury.

19. The electrically controlled suction regulator of claim 11, wherein said source of vacuum is a distributed hospital vacuum system.

20. A method of electrically controlling a suction regulator, comprising the steps of:
providing a source of vacuum;
converting said source of vacuum to a source of electrical current;
providing a regulated source of vacuum;
providing an electrically controlled valve having an input connected to said regulated source of vacuum and having an output which is a source of suction to be controlled; and
controlling said electrically controlled valve by means of circuitry which converts said electrical current to signals for operating said electrically controlled valve such that said regulated source of suction is supplied to a patient for predetermined periods of time.

21. The method of claim 20, further including the step of providing an alarm when suction being applied to said patient is obstructed.

22. The electronically controlled suction regulator of claim 10, wherein said pressure transducer is connected to provide an output signal to said electronic circuitry.

* * * * *